(12) United States Patent
Sugawara (10) Patent No.: US 9,226,647 B2
(45) Date of Patent: Jan. 5, 2016

(54) ENDOSCOPIC APPARATUS AND OPERATION CONTROL METHOD FOR THE SAME

(71) Applicant: OLYMPUS CORPORATION, Tokyo (JP)

(72) Inventor: Tateyuki Sugawara, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 310 days.

(21) Appl. No.: 13/801,760

(22) Filed: Mar. 13, 2013

(65) Prior Publication Data

US 2013/0197308 A1    Aug. 1, 2013

Related U.S. Application Data

(63) Continuation of application No. PCT/JP2011/071873, filed on Sep. 26, 2011.

(30) Foreign Application Priority Data

Sep. 30, 2010   (JP) ................................ 2010-222840

(51) Int. Cl.
*A61B 1/00*    (2006.01)
*A61B 1/04*    (2006.01)
(Continued)

(52) U.S. Cl.
CPC ........... *A61B 1/00131* (2013.01); *A61B 1/0051* (2013.01); *A61B 1/00096* (2013.01);
(Continued)

(58) Field of Classification Search
CPC .......... A61B 1/12; A61B 1/121; A61B 1/126; A61B 1/127; A61B 1/0008; A61B 1/00096; A61B 1/00043; A61B 1/00055

USPC .......... 600/109, 118, 129, 160, 169, 176, 177
See application file for complete search history.

(56) References Cited

U.S. PATENT DOCUMENTS 4,870,950 A * 10/1989 Kanbara et al. ............... 600/109
4,924,852 A *  5/1990 Suzuki et al. .................. 600/150
(Continued)

FOREIGN PATENT DOCUMENTS

CN    1141505 A    1/1997
EP    2 110 070 A1    10/2009
(Continued)

OTHER PUBLICATIONS

International Search Report dated Dec. 13, 2011 issued in corresponding International Application No. PCT/JP2011/071873.
(Continued)

*Primary Examiner* — Anhtuan T. Nguyen
*Assistant Examiner* — William Chou
(74) *Attorney, Agent, or Firm* — Scully, Scott, Murphy & Presser, P.C.

(57) ABSTRACT

An endoscopic apparatus includes an ultrasonic vibrator, a diffraction grating, an electrical energy generator, a detector, a determination unit, a controller. The diffraction grating converts the ultrasonic vibration into a surface acoustic wave propagating on a surface of the transparent member. The detector detects reflected electrical energy reflected from the energy supply system. The determination unit determines whether the electrical energy suitable to drive the ultrasonic vibrator has been supplied to the ultrasonic vibrator based on the reflected electrical energy detected by the detector. The controller controls the electrical energy output from the signal generator based on a determination result of the determination unit.

13 Claims, 5 Drawing Sheets

(51) Int. Cl.
  *A61B 1/12* (2006.01)
  *A61B 1/06* (2006.01)
  *A61B 1/005* (2006.01)
  *A61B 8/12* (2006.01)
  *G02B 23/24* (2006.01)
  *A61B 1/07* (2006.01)

(52) U.S. Cl.
  CPC . *A61B1/126* (2013.01); *A61B 8/12* (2013.01); *G02B 23/2423* (2013.01); *G02B 23/2476* (2013.01); *G02B 23/2484* (2013.01); *A61B 1/07* (2013.01)

(56) References Cited

U.S. PATENT DOCUMENTS

| | | | | |
|---|---|---|---|---|
| 5,042,460 | A * | 8/1991 | Sakurai et al. | 606/128 |
| 5,351,677 | A * | 10/1994 | Kami et al. | 600/109 |
| 5,387,190 | A * | 2/1995 | Gotanda et al. | 604/22 |
| 7,896,804 | B2 * | 3/2011 | Uchimura et al. | 600/173 |
| 2008/0188714 | A1 * | 8/2008 | McCaffrey | 600/157 |
| 2008/0319266 | A1 * | 12/2008 | Poll et al. | 600/157 |
| 2009/0264701 | A1 | 10/2009 | Ito | |
| 2011/0082336 | A1 * | 4/2011 | Ito | A61B 1/00091 600/129 |

FOREIGN PATENT DOCUMENTS

| | | |
|---|---|---|
| EP | 2 305 099 A1 | 4/2011 |
| JP | 2006-055275 | 3/2006 |
| JP | 2009-254571 | 11/2009 |

OTHER PUBLICATIONS

International Preliminary Report on Patentability together with the Written Opinion dated Apr. 18, 2013 received in related International Application No. PCT/JP2011/071873.

Chinese Office Action dated Sep. 30, 2014 from related Chinese Application No. 201180046073.9, together with an English language translation.

Extended Supplementary European Search Report dated Mar. 16, 2015 from related European Application No. 11 82 9022.0.

European Patent Communication dated Sep. 3, 2015, from corresponding European Application No. 11 829 022.0.

* cited by examiner

ENDOSCOPIC APPARATUS AND OPERATION CONTROL METHOD FOR THE SAME

CROSS REFERENCE TO RELATED APPLICATIONS

This application is a Continuation Application of PCT Application No. PCT/JP2011/071873, filed Sep. 26, 2011 and based upon and claiming the benefit of priority from prior Japanese Patent Application No. 2010-222840, filed Sep. 30, 2010, the entire contents of all of which are incorporated herein by reference.

BACKGROUND OF THE INVENTION

1. Field of the Invention

The present invention relates to an endoscopic apparatus in which a diffraction grating is arranged on a transparent member such as a cover glass provided at the distal end of the endoscopic apparatus, and contamination on the transparent member is removed by applying ultrasonic vibration to the transparent member by means of a piezoelectric vibrator, thereby propagating a surface acoustic wave across the transparent member, and an operation control method for the same.

2. Description of the Related Art

When the distal end of an endoscopic apparatus (hereinafter, simply referred to as the distal end) is inserted into a body cavity during surgery, contamination such as body fluids or droplets produced by the use of an RF knife may adhere to a cover glass provided at the distal end. To remove this contamination, there are well-known techniques of imparting the vibrations of an ultrasonic vibrator to the cover glass to cause a surface acoustic wave to propagate. Such a technique is taught in Jpn. Pat. Appln. KOKAI Publication No. 2006-055275, for example, which discloses that a cover glass is provided at a distal end, and ultrasonic vibration is induced in the cover glass by imparting oscillations from an ultrasonic vibrator, thereby removing contamination from the cover glass.

In the technique of removing contamination from a cover glass by using a surface acoustic wave obtained by the application of ultrasonic vibration, an ultrasonic vibrator must be driven at high power in the range of several watts to several tens of watts. In a conventional endoscopic apparatus using a piezoelectric vibrator as the ultrasonic vibrator, high power is supplied to the piezoelectric vibrator without taking into account the driving state of the piezoelectric vibrator or the state of transmission of the surface acoustic wave.

BRIEF SUMMARY OF THE INVENTION

An endoscopic apparatus according to aspect of the present invention comprises a transparent member provided at a distal end portion, an ultrasonic vibrator provided in the transparent member and configured to generate ultrasonic vibration; an electrical energy generator configured to supply electric energy to drive the ultrasonic vibrator and generate the ultrasonic vibration; a diffraction grating provided in the transparent member and configured to impart the ultrasonic vibration generated by the ultrasonic vibrator to the transparent member and convert the ultrasonic vibration into a surface acoustic wave propagating on a surface of the transparent member; an energy supply system including the ultrasonic vibrator and a path for supplying the electrical energy to the ultrasonic vibrator among the electrical energy supplied to the ultrasonic vibrator; a detector configured to detect reflected electrical energy reflected from the energy supply system; a determination unit configured to determine whether the electrical energy suitable to drive the ultrasonic vibrator has been supplied to the ultrasonic vibrator based on the reflected electrical energy detected by the detector; and a controller configured to control the electrical energy output from the signal generator based on a determination result of the determination unit.

A method of operation control of an endoscopic apparatus according to aspect of the present invention comprises: supplying electrical energy to an ultrasonic vibrator provided in a transparent member at a distal end portion to generate ultrasonic vibration and impart the ultrasonic vibration to the transparent member; converting, by a diffraction grating provided in the transparent member, the ultrasonic vibration to a surface acoustic wave propagating on a surface of the transparent member; detecting reflected electrical energy reflected from an energy supply system including the ultrasonic vibrator and a path for supplying the electrical energy to the ultrasonic vibrator among the electrical energy supplied to the ultrasonic vibrator; determining whether the electrical energy suitable to drive the ultrasonic vibrator has been supplied to the ultrasonic vibrator based on the detected reflected electrical energy; and controlling the electrical energy output from the signal generator based on a determination result.

DETAILED DESCRIPTION OF THE INVENTION

A description will now be given of an endoscopic apparatus according to an embodiment, with reference to the drawings.

Figure 1:
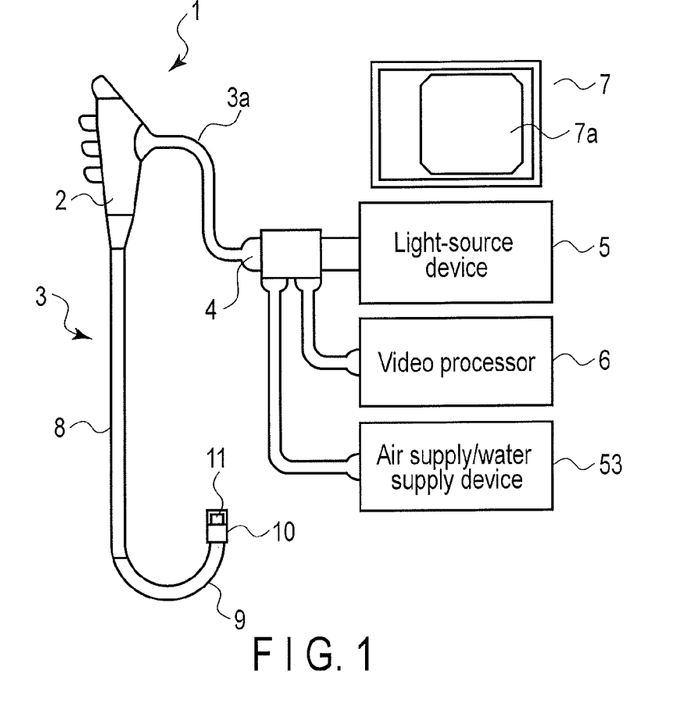
FIG. 1 is a diagram showing the overall configuration of an endoscopic apparatus according to an embodiment of the invention.

FIG. 1 is a diagram showing the overall configuration of an endoscopic apparatus. The endoscopic apparatus includes an endoscope 1, a light-source device 5, a video processor 6 and a monitor 7. The endoscope 1 picks up an image of a subject, such as a body cavity. The light-source device 5 emits light toward the endoscope 1 so that the endoscope 1 picks up an image of the subject. The video processor 6 performs a predetermined image processing to an image signal transmitted from the endoscope 1 and creates an observation image corresponding to the image signal. The monitor 7 displays the observation image created by the video processor 6.

The endoscope 1 includes an operation portion 2, an insertion portion 3, and a universal cord 3a. The operation portion 2 performs bending operation of a bendable portion 9 of the insertion portion 3 or control of the ducting. The operation portion 2 includes an operation knob for remotely bending the bendable unit 9. The insertion portion 3 is formed into a cylindrical shape. An operation wire (not shown in the drawings) is inserted into the insertion portion 3. By operating the operation knob, the operation wire (not shown in the drawings) inserted into the insertion portion 3 is tightened or loosened. By so doing, the bendable portion 9 is bendable in multiple directions. The operation portion 2 is connected to the proximal end of the insertion portion 3, and the insertion portion 3 is inserted into the body cavity from the distal end.

The universal cord 3a extends from the operation portion 2. A connector portion 4 is provided at the distal end of the universal cord 3a. The connector portion 4 is connected to both of the light-source device 5 and the video processor 6 by means of a connector having a predetermined structure.

The insertion portion 3 includes a tube 8, the bendable portion 9 and a distal end portion 10. The tube 8 is formed of a flexible material. The bendable portion 9 is provided at the distal end of the tube 8. The distal end portion 10 is formed in a cylindrical shape and provided at the distal end of the bendable portion 9. The distal end portion 10 includes an imaging element 11 to pick up an image of a part such as the body cavity, for example.

The imaging element 11 picks up an image of a part such as the body cavity, for example and outputs an image signal. The image signal output from the imaging element 11 is transmitted to the video processor 6 through the universal cord 3a. The video processor 6 is connected to the monitor 7. The monitor 7 comprises a display screen 7a.

The video processor 6 processes the image signal transmitted from the imaging element 11 to generate an observation image signal of the part picked up by the imaging element 11 and displays an observation image on the display screen 7a of the monitor 7.

Figure 2:
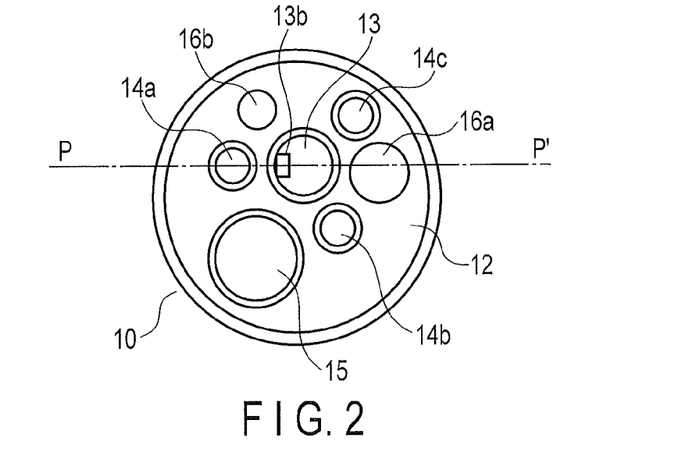
FIG. 2 is a front view of the distal end of the insertion portion of the endoscope of the apparatus looking toward the distal end.
Figure 3:
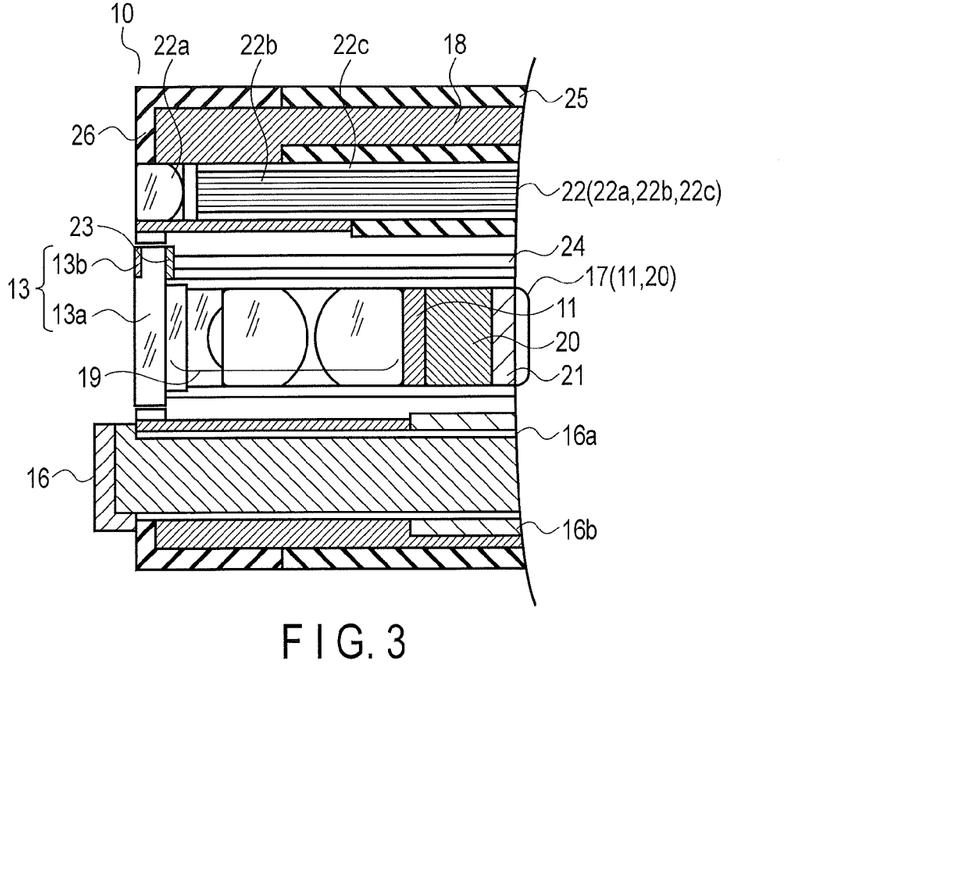
FIG. 3 is a sectional view of the distal end of the insertion portion, taken along line P-P' shown in FIG. 2.

FIG. 2 is a front view of the distal end portion 10 looking toward the distal end portion, and FIG. 3 is a sectional view of the distal end portion 10, taken along line P-P' shown in FIG. 2. A distal end surface 12 of the distal end portion 10 has an observation window 13, a diffraction grating 13b, three illumination windows 14a, 14b and 14c, an opening 15 from which a surgical instrument is inserted, and a water supply nozzle 16 (16a, 16b). The distal end surface 12 of the distal end portion 10 defines a plurality of openings for the observation window 13, the three illumination windows 14a, 14b and 14c, the opening 15 for a surgical instrument and the water supply nozzle 16.

A transparent member 13a that covers the observation window 13 is attached to the observation window 13. The diffraction grating 13b is provided on the outer surface of the transparent member 13a, i.e., the exterior of the distal end portion 10. The diffraction grating 13b comprises a plurality of linear grooves arranged parallel to one another. The cross section of the diffraction grating 13b is rectangular.

The water supply nozzle 16 cleans blood, mucus or the like of the affected portion of the subject by supplying water.

As shown in FIG. 2, the three illumination windows 14a, 14b and 14c are provided on the distal end surface 12 of the distal end portion 10. Illumination windows 14a, 14b and 14c are equidistantly separated from each other on the circle whose center is coincident with the optical axis of the observation window 13. The three illumination windows 14a, 14b and 14c are provided on a plane orthogonal to the optical axis of the observation window 13. One of the opening 15 for a surgical instrument and the water supply nozzle 16 and one of illumination windows 14a, 14b and 14c are alternately provided. The opening 15 for a surgical instrument and the water supply nozzle 16 are arranged on the circle whose center is coincident with the optical axis of the observation window 13.

Concretely, the opening 15 for a surgical instrument is provided between illumination windows 14a and 14b, the water supply nozzle 16a is provided between illumination windows 14b and 14c, and the water supply nozzle 16b is provided between illumination windows 14a and 14c. Each of three windows for providing the opening 15 for a surgical instrument and the water supply nozzles 16a and 16b is provided between illumination windows 14a, 14b and 14c.

As shown in FIG. 3, a distal end solid portion 18 is provided in the distal end portion 10. The distal end solid portion 18 has space for providing an image pick-up unit 17 and a light guide unit 22 inside the distal end portion 10. The image pick-up unit 17 is opposed to the observation window 13. The light guide unit 22 is opposed to an illumination lens 22a. An illumination lens 22a is arranged corresponding to each of the three illumination windows 14a, 14b and 14c.

The distal end of the distal end solid portion 18 is covered with a cap 26.

The transparent member 13a is provided at the distal end of the image pick-up unit 17. The image pick-up unit 17 is inserted into the distal end solid portion 18 and fixed so that the transparent member 13a is placed in correspondence with the observation window 13 of the distal end portion 10.

An observation optical system 19 includes a plurality of lens arranged on the inner surface of the transparent member 13a. The imaging element 11 is formed of a solid-state image sensing device such as a CCD image sensor or a CMOS image sensor. The image pick-up unit 17 includes a substrate 20 including various circuits. The imaging element 11 is connected to each circuit on the substrate 20. The substrate 20 is connected to a signal cable 21. The signal cable 21 is connected to the video processor 6 through the insertion portion 3. The image pick-up unit 17 is fixed to the distal end solid portion 18 by means of a filler not shown in the drawings.

The light guide unit 22 includes an illumination lens 22a and an optical fiber bundle 22b which is a light guide. The light guide unit 22 emits light toward a subject of the part such as the body cavity. The distal end portion 10 has space for providing the light guide unit 22 inside thereof. In the space inside of the distal end portion 10, a metallic pipe 22c is provided. The distal end of the optical fiber bundle 22b is fixed inside the metallic pipe 22c by an adhesive or the like. The light guide unit 22 is fixed to the distal end solid portion 18 by a fixing screw. A part of the metallic pipe 22c and the optical fiber bundle 22b are covered with an outer covering tube 25.

The distal end of the water supply nozzle 16 has an opening. The opening is provided so that water issues from the water supply nozzle 16 in the direction parallel to the plane orthogonal to the optical axis of the image pick-up unit 17. The proximal end of the water supply nozzle 16 is formed in a pipe shape and is connected to a water supply tube 16b by a connecting pipe 16a. The water supply path includes the connecting pipe 16a and the water supply tube 16b.

A piezoelectric vibrator 23 functioning as an ultrasonic vibrator is attached to the inner surface of the transparent member 13a, i.e., the inside of the distal end portion 10. The piezoelectric vibrator 23 is attached to the diffraction grating 13b by means of the transparent member 13a. The piezoelectric vibrator 23 generates ultrasonic vibration by receiving power which is electrical energy.

Figure 4:
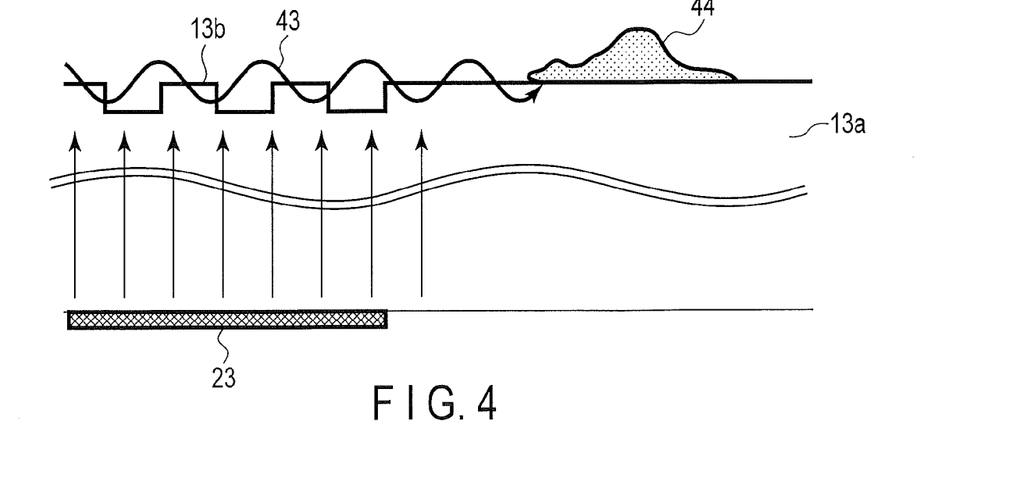
FIG. 4 shows a simulation for removing contamination by generating ultrasonic vibration in the apparatus.

Ultrasonic vibration generated by the piezoelectric vibrator 23 is mainly propagated in the direction perpendicular to the surface on which the piezoelectric vibrator 23 is attached and induced into the diffraction grating 13b arranged opposed to the piezoelectric vibrator 23. The ultrasonic vibration induced to the diffraction grating 13b is changed to a surface acoustic wave 43 propagating on the outer surface of the transparent member 13a by the diffraction grating 13b. The surface acoustic wave 43 removes contamination 44 on the transparent member 13a when the wavefront reaches the contamination 44.

The wavelength λ of the diffraction grating 13b is given by λ=v/f, wherein v represents the velocity of the surface acoustic wave 43 propagating the transparent member 13a, and f represents the frequency of ultrasonic vibration.

FIGS. 1 to 3 indicate the structures roughly, and the dimensional ratios are not accurate.

Figure 5:
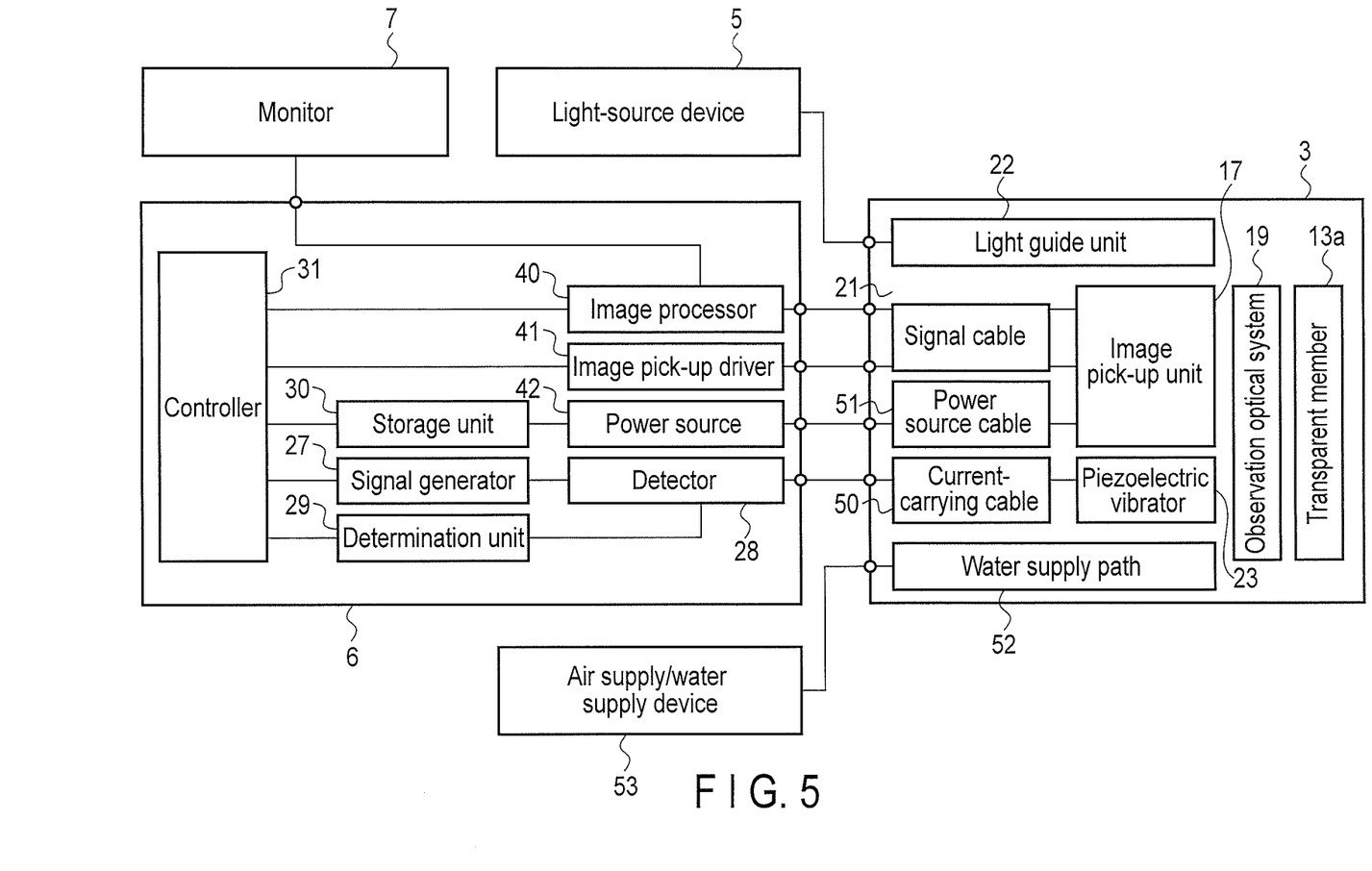
FIG. 5 is a functional block in the apparatus.

FIG. 5 is a block diagram showing the functions of the endoscopic apparatus. The video processor 6 includes a controller 31. The controller 31 is connected to an image processor 40, an image pick-up driver 41, a storage unit 30, a signal generator (electrical energy generator) 27 and a determination unit 29. The controller 31 controls operations of the image processor 40, the image pick-up driver 41, the signal generator 27 and the determination unit 29. The controller 31 writes to and reads from the storage unit 30. The video processor 6 is provided with a power source 42, and is connected to the monitor 7.

In the insertion portion 3, the transparent member 13a, the observation optical system 19, the image pick-up unit 17, the piezoelectric vibrator 23, light guide unit 22 and a water supply path 52. The image pick-up unit 17 includes the imaging element 11. The image pick-up unit 17 is connected to the image pick-up driver 41 and the image processor 40 of the video processor 6 through the signal cable 21. The image pick-up unit 17 is connected to the power source 42 of the video processor 6 through a power source cable 51. The piezoelectric vibrator 23 is connected to a detector 28 of the video processor 6 through a current-carrying cable 50. The current-carrying cable 50 supplies AC power to the piezoelectric vibrator 23 to drive the piezoelectric vibrator 23. The electrical energy to be supplied to and reflected from the piezoelectric vibrator 23 is transmitted through the current-carrying cable 50. The light guide unit 22 is connected to the light-source device 5. The water supply path 52 comprises an air supply/water supply device 53.

Concretely, the image pick-up driver 41 transmits a driving signal to the image pick-up unit 17 through the signal cable 21. The imaging element 11 of the image pick-up unit 17 picks up an image of a part such as the body cavity and outputs an image signal upon reception of the driving signal from the image pick-up driver 41. The image signal output from the imaging element 11 is transmitted to the image processor 40 through the signal cable 21. The image processor 40 processes the image signal transmitted from the imaging element 11, generates an observation image signal and outputs an observation image on the display screen 7a of the monitor 7. The light-source device 5 emits light for picking up an image of the subject by the endoscope 1 to the light guide unit 22. The light guide unit 22 emits light from the light-source device toward the subject of a part such as the body cavity. The air supply/water supply device 53 blows air and supplies water into the water supply path 52 of the insertion portion 3.

The signal generator 27 supplies AC power to the piezoelectric vibrator 23 as electrical energy so that the piezoelectric vibrator 23 is driven and generates ultrasonic vibration. The signal generator 27 generates AC power. The AC power generated from the signal generator 27 is supplied to the piezoelectric vibrator 23 through the detector 28 and the current-carrying cable 50.

The detector 28 extracts electrical energy reflected on the path including the piezoelectric vibrator 23 and the current-carrying cable 50 from the AC power supplied to the piezoelectric vibrator 23, i.e., a power (reflected power) reflected from the supplement system as an DC voltage.

Figure 6:
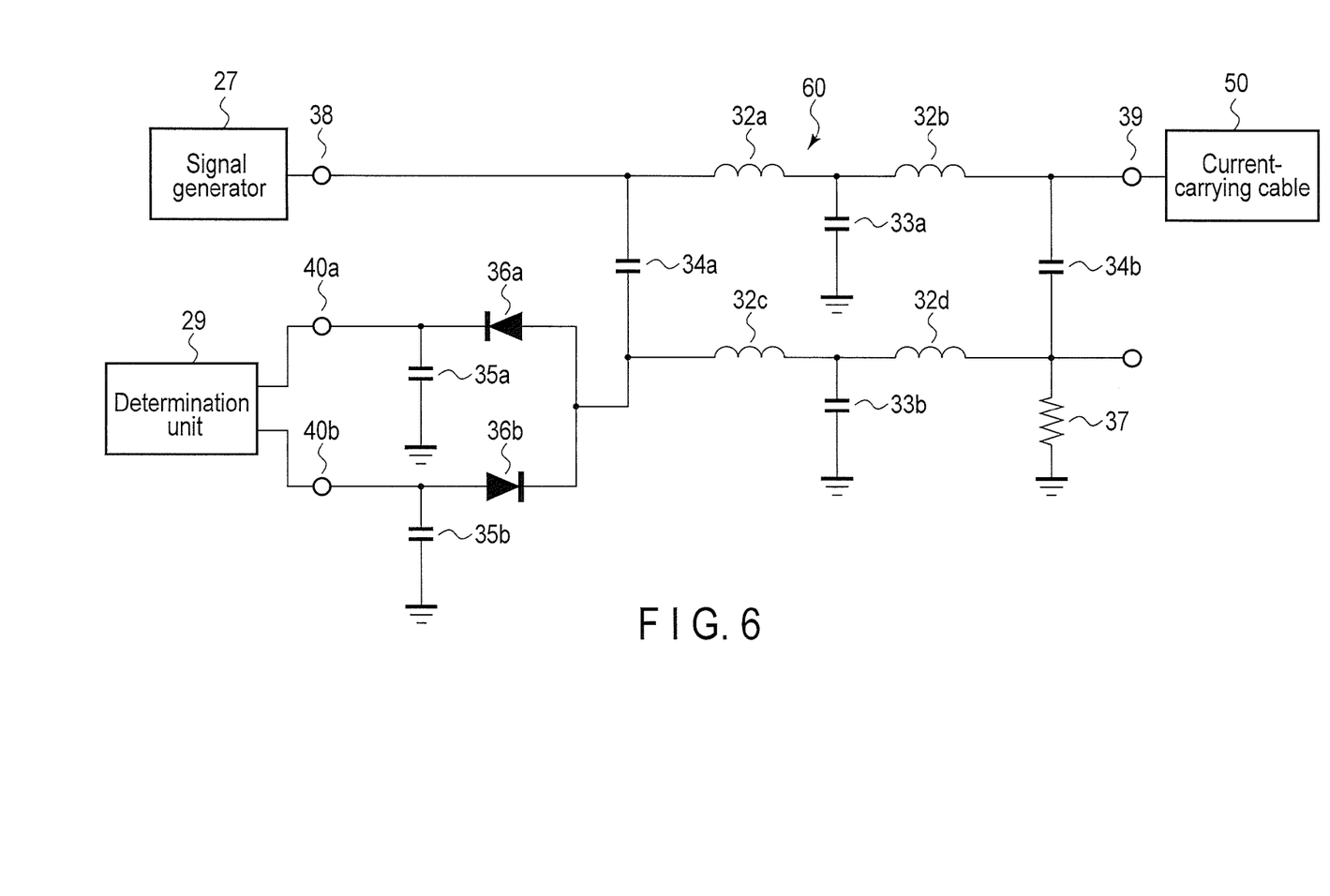
FIG. 6 shows a circuit structure of the detection portion in the apparatus.

FIG. 6 shows the circuit structure of the detector 28. A first port 38 is connected to the signal generator 27. A coupling circuit 60 is connected between the first port 38 and a second port 39. The coupling circuit 60 supplies the AC power output from the signal generator 27 to the piezoelectric vibrator 23 through current-carrying cable 50 and extracts the AC reflected power reflected from the path including the piezoelectric vibrator 23.

Concretely, the coupling circuit 60 includes a plurality of inductors 32a, 32b, 32c and 32d, a plurality of capacitors 33a, 33b, 34a and 34b and a resistor 37. Inductors 32a and 32b are connected between the first port 38 and second port 39 in series. Inductors 32c and 32d are connected in series. Each of the ends of the pair of inductors 32c and 32d is connected to each of the ends of the pair of inductors 32a and 32b by means of capacitors 34a and 34b, respectively. Capacitor 33a is connected between the pair of inductors 32a and 32b, and capacitor 33b is connected between the pair of inductors 32c and 32d. A diode 36a is connected between capacitor 34a and capacitor 35a in the forward direction, and a diode 36b is connected between capacitor 34a and capacitor 35b in the reverse direction. Diodes 36a and 36b are connected to the determination unit 29. Diode 36a is connected to capacitor 35a in parallel, and diode 36b is connected to capacitor 35b in parallel.

In the coupling circuit 60, a grounded inductor may be connected between capacitor 34a and each of diodes 36a and 36b, or between inductor 32c and each of diodes 36a and 36b to effectively extract the reflected power from the path including the piezoelectric vibrator 23. Similarly, in the coupling circuit 60, a grounded resistor may be connected between diode 36a and capacitor 35a or between diode 36b and capacitor 35b.

With the above structure, the AC power output from the signal generator 27 passes through each of inductors 32a and 32b of the detector 28 and is supplied to the piezoelectric vibrator 23 through the current-carrying cable 50. The reflected power reflected from the piezoelectric vibrator 23 is returned to the detector 28 through the current-carrying cable 50. In this case, the reflected power can be detected by a packing effect of the impedance elements including the plurality of inductors 32a, 32b, 32c and 32d, the plurality of capacitors 33a, 33b, 34a and 34b and the resistor 37 within the detector 28. That is, the reflected power reflected from the piezoelectric vibrator 23 is transmitted to each of diodes 36a and 36b and each of capacitors 35a and 35b by means of the plurality of capacitors 34a and 34b. The AC reflected power is converted to a voltage according to the reflected power by each of diodes 36a and 36b and each of capacitors 35a and 35b. The voltage according to the reflected power is transmitted to the determination unit 29.

The determination unit 29 determines whether the AC power suitable to drive the piezoelectric vibrator 23 has been supplied to the piezoelectric vibrator 23 based on the voltage transmitted from the detector 28, and whether a fault occurs in the path. Concretely, the determination unit 29 compares the voltage according to the reflected power detected by the detector 28 with a predetermined threshold, and determines whether or not the voltage according to the reflected power is greater than or equal to the threshold.

The storage unit 30 stores the determination results of the determination unit 29 such as the increased or decreased amount of AC power output from the signal generator 27, and the log of stopping the output of AC power from the signal generator 27. The storage unit 30 prestores a threshold used for comparison with the voltage according to the reflected power detected by the detector 28 performed in the determination unit 29. The storage unit 30 stores an operation control program the present apparatus.

The operation control program includes a detection function for generating AC power from the signal generator 27 and detecting a reflected power reflected from the path including the piezoelectric vibrator 23 among power supplied to the piezoelectric vibrator 23, a determination function for determining whether the AC power suitable to drive the piezoelectric vibrator 23 has been supplied to the piezoelectric vibrator 23 based on the detected reflected power, and a control function for controlling the AC power output from the signal generator 27 based on the determination results.

The determination function compares the reflected power with the predetermined threshold.

If the determination function determines that the reflected power is greater than or equal to the threshold, the control function stops output of the AC power from the signal generator 27, on the assumption that an unexpected situation has occurred in one of or both of the piezoelectric vibrator 23 and the current-carrying cable 50.

The controller 31 executes the operation control program stored in the storage unit 30 and controls the operations of the image processor 40, the image pick-up driver 41, the signal generator 27, the determination unit 29 and storage unit 30.

The controller 31 increases or decreases the AC power output from the signal generator 27 based on the determination results of the determination unit 29. If the determination unit 29 determines that the voltage according to the reflected power is greater than or equal to the threshold, the controller 31 stops output of the AC power from the signal generator 27, on the assumption that an unexpected situation, such as open- or short-circuit of the current-carrying cable 50 has occurred in one of or both of the piezoelectric vibrator 23 and the current-carrying cable 50.

The controller 31 indicates that the output of AC power from the signal generator 27 is stopped on the monitor 7 when the output of AC power from the signal generator 27 is stopped.

The controller 31 stores at least the determination results of the determination unit 29 such as the increased or decreased amount of AC power output from the signal generator 27, and the log of stopping the output of AC power from the signal generator 27 in the storage unit 30.

Figure 7:
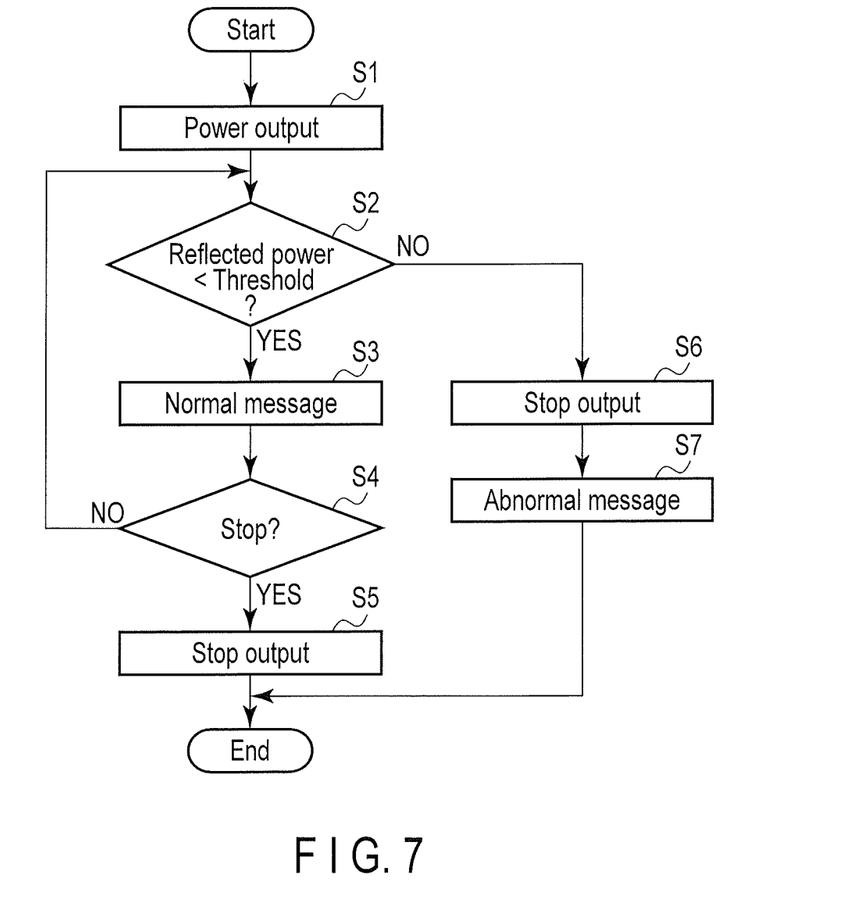
FIG. 7 is a flowchart for operation control in the apparatus.

Next, the operation of the aforementioned apparatus with reference to the operation control flowchart shown in FIG. 7.

In step S1, the controller 31 outputs an instruction for outputting AC power to the signal generator 27. The signal generator 27 supplies the AC power to piezoelectric vibrator 23 to drive the piezoelectric vibrator 23 and generate ultrasonic vibration upon reception of the instruction from the controller 31. The signal generator 27 generates the AC power. The AC power output from the signal generator 27 passes through each of inductors 32a and 32b of the detector 28 shown in FIG. 6 and is supplied to the piezoelectric vibrator 23 through the current-carrying cable 50. AC reflected power is generated in the piezoelectric vibrator 23. The reflected power reflected from the path including the piezoelectric vibrator 23 is returned to the detector 28 through the current-carrying cable 50. The detector 28 detects the reflected power by a packing effect of the impedance elements including the plurality of inductors 32a, 32b, 32c and 32d, the plurality of capacitors 33a, 33b, 34a and 34b and the resistor 37. That is, the reflected power reflected from the piezoelectric vibrator 23 is transmitted to each of diodes 36a and 36b and each of capacitors 35a and 35b by means of the plurality of capacitors 34a and 34b. The AC reflected power is converted into a voltage according to the reflected power by each of diodes 36a and 36b and each of capacitors 35a and 35b. The voltage according to the reflected power is transmitted to the determination unit 29.

In step S2, the determination unit 29 compares the voltage according to the reflected power detected by the detector 28 with a predetermined threshold, and determines whether or not the voltage according to the reflected power is greater than or equal to the threshold. As a result of the comparison, if the voltage according to the reflected power is less than or equal to the threshold, the determination unit 29 report it to the controller 31.

In step S3, the controller 31 displays a normal message indicating that the AC power suitable to drive the piezoelectric vibrator 23 has been supplied to the piezoelectric vibrator 23 on the monitor 7. The determination unit 29 transmits power information corresponding to the voltage according to the reflected power to the controller 31. The controller 31 increases or decreases the AC power output from the signal generator 27 in accordance with the power information obtained at the determination unit 29.

In step S4, the controller 31 determines whether or not a stop instruction is received by a manual operation of the operation portion 2 or the like. As a result of the determination, if such an instruction is not received, the controller 31 returns to step S2. If a stop instruction is received, the controller 31 moves to step S5 and stops generation of AC power of the signal generator 27 and as a result, the driving operation of the piezoelectric vibrator 23 is terminated.

The piezoelectric vibrator 23 may lose the initial characteristics because of aging. In such a case, the impedance of the piezoelectric vibrator 23 changes, and impedance mismatch occurs. Accordingly, the reflected power from the piezoelectric vibrator 23 becomes large. If the reflected power from the piezoelectric vibrator 23 becomes large, the voltage according to the reflected power detected by the detector 28 will exceed the threshold.

In this case, the determination unit 29 determines that the voltage according to the reflected power detected by the detector 28 is greater than or equal to the threshold and reports it to the controller 31 as in step S2.

The controller 31 moves from step S2 to step S6 and stops output of the AC power from the signal generator 27.

In step S7, the controller 31 displays an abnormal message indicating that the output of AC power from the signal generator 27 is stopped on the monitor 7.

There is a case where an unexpected situation, such as open- or short-circuit of the current-carrying cable 50 has occurred in a path for supplying power to the piezoelectric vibrator 23. In this case, the reflected power will become large. If the reflected power becomes large, the voltage according to the reflected power detected by the detector 28 will exceed the threshold. Then, the determination unit 29 determines that the voltage according to the reflected power detected by the detector 28 is greater than or equal to the threshold and reports it to the controller 31 as in step S2.

The controller 31 moves from step S2 to step S6 and stops the output of AC power from the signal generator 27.

In step S7, the controller 31 displays an abnormal message indicating that the output of AC power from the signal generator 27 is stopped on the monitor 7.

The controller 31 may display the reason for stopping the output of AC power from the signal generator 27. The reason may include that the piezoelectric vibrator 23 has lost the initial characteristics because of aging, and an unexpected situation, such as open- or short-circuit has occurred in the current-carrying cable 50.

According to the aforementioned embodiment, the reflected power reflected from the piezoelectric vibrator 23 and the current-carrying cable 50 supplying AC power to the piezoelectric vibrator 23 is detected, whether or not the AC power suitable to drive the piezoelectric vibrator 23 is supplied to the piezoelectric vibrator 23 is determined based on the reflected power, and the AC power output from the signal generator 27 is controlled based on the determination results. For example, if the determination unit 29 determines that the reflected power is greater than or equal to the threshold, the controller 31 stops output of the AC power from the signal generator 27, on the assumption that an unexpected situation has occurred in one of or both of the piezoelectric vibrator 23 and the current-carrying cable 50.

By the above procedure, the driving state of the piezoelectric vibrator 23 is monitored so that the piezoelectric vibrator 23 can be suitably driven. This procedure allows early detection of a fault in the path including the current-carrying cable 50 and improves safety. That is, it is possible to recognize whether the piezoelectric vibrator 23 has lost the initial characteristics because of aging, or an unexpected situation, such as open- or short-circuit has occurred in the current-carrying cable 50 based on the monitor 7. Concretely, it is possible to realize early detection of a fault in the path including the current-carrying cable 50 for supplying high power to the piezoelectric vibrator 23, such as disconnection or short-circuiting, or a fault such as damage to the piezoelectric vibrator 23, and correct such a fault earlier.

The embodiment of the present invention has been hereinabove explained. However this embodiment is presented as an example, and is not intended to limit the scope of the invention. Further embodiments can be embodied in various other forms, and various omissions, replacements, and changes can be made without deviating from the gist of the invention. The embodiment and the modifications thereof are included in the scope and the gist of the invention.

For example, detecting the reflected power reflected from the piezoelectric vibrator 23 and the current-carrying cable 50 supplying AC power to the piezoelectric vibrator 23, determining whether or not AC power suitable to drive the piezoelectric vibrator 23 is supplied to the piezoelectric vibrator 23 based on the reflected power, and controlling the AC power output from the signal generator 27 based on the determination results may be performed after the apparatus is turned on, and the insertion portion 3 of the apparatus is inserted into the subject such as the body cavity and before the apparatus is used.

What is claimed is:

1. An endoscopic apparatus comprising:
   an electrical energy generator configured to generate electrical energy;
   an ultrasonic vibrator electrically connected to the electrical energy generator, wherein the ultrasonic vibrator is configured to be driven by the electrical energy to generate ultrasonic vibration;
   a light transmitting optical member defining a diffraction grating on an outer surface of the light transmitting optical member,
      wherein the light transmitting optical member is configured to propagate the ultrasonic vibration generated by the ultrasonic vibrator to the diffraction grating, and
      wherein the diffraction grating is configured to change the ultrasonic vibration to a surface acoustic wave propagating on the outer surface of the light transmitting optical member;
   a detector comprising a coupling circuit electrically connected to the electrical energy generator and the ultrasonic vibrator, wherein the coupling circuit is configured to:
      supply the electrical energy to the ultrasonic vibrator to drive the ultrasonic vibrator to generate the ultrasonic vibration; and
      during the supply of the electrical energy to the ultrasonic vibrator to drive the ultrasonic vibrator to generate the ultrasonic vibration, detect reflected electrical energy reflected from the ultrasonic vibrator;
   a determination circuit configured to make a determination of whether the electrical energy is suitable to drive the ultrasonic vibrator based on the reflected electrical energy reflected from the ultrasonic vibrator detected by the coupling circuit of the detector; and
   a controller configured to control the electrical energy generator to generate the electrical energy based on the determination made by the determination circuit.

2. The endoscopic apparatus of claim 1, wherein the controller is configured to control the electrical energy generator to increase, decrease or stop generation of the electrical energy based on the determination made by the determination circuit.

3. The endoscopic apparatus of claim 2,
   wherein the determination circuit is configured to make the determination of whether the electrical energy is suitable to drive the ultrasonic vibrator by comparing the reflected electrical energy with a predetermined threshold, and
   wherein the controller is configured to control the electrical energy generator to increase or decrease generation of the electrical energy in accordance with the determination made by the determination circuit.

4. The endoscopic apparatus of claim 2,
   wherein the determination circuit is configured to make the determination of whether the electrical energy is suitable to drive the ultrasonic vibrator by comparing the reflected electrical energy with a predetermined threshold, and
   wherein the controller is configured to control the electrical energy generator to stop generation of the electrical energy when the determination circuit determines that the reflected electrical energy is greater than or equal to the predetermined threshold.

5. The endoscopic apparatus of claim 4, further comprising:
   a monitor,
   wherein the controller is configured to control the monitor to display a message indicating that generation of the electrical energy by the electrical energy generator is stopped.

6. The endoscopic apparatus of claim 1, further comprising:
   a storage,
   wherein the controller is configured to control the storage to store a log of the determination made by the determination circuit.

7. The endoscopic apparatus of claim 1, wherein the ultrasonic vibrator comprises a piezoelectric vibrator.

8. The endoscopic apparatus of claim 1, wherein the electrical energy is electric power.

9. The endoscopic apparatus of claim 1, wherein the light transmitting optical member is formed of a glass material.

10. The endoscopic apparatus of claim 1, further comprising:

a cable as a path through which the electrical energy generated by the electrical energy generator is supplied to the ultrasonic vibrator, and the reflected electrical energy from the ultrasonic vibrator is supplied to the coupling circuit of the detector, wherein the determination circuit is configured to make the determination of whether the electrical energy is suitable to drive the ultrasonic vibrator by comparing the reflected electrical energy with a predetermined threshold, and wherein the controller is configured to control the electrical energy generator to stop generation of the electrical energy when the determination circuit determines that the reflected electrical energy is greater than or equal to the predetermined threshold.

11. The endoscopic apparatus of claim 10,
wherein the detector is electrically connected between the electrical energy generator and the cable, and
wherein the coupling circuit is configured to supply the electrical energy generated by the electrical energy generator to the cable and to convert the reflected electrical energy supplied through the cable into DC power in accordance with the reflected electrical energy.

12. A method of controlling an endoscopic apparatus, the method comprising:
generating electrical energy by an electrical energy generator;
driving an ultrasonic vibrator electrically connected to the electrical energy generator, wherein the ultrasonic vibrator is driven by the electrical energy to generate ultrasonic vibration;
providing a light transmitting optical member defining a diffraction grating on an outer surface of the light transmitting optical member,
wherein the light transmitting optical member propagates the ultrasonic vibration generated by the ultrasonic vibrator to the diffraction grating, and
wherein the diffraction grating changes the ultrasonic vibration to a surface acoustic wave propagating on the outer surface of the light transmitting optical member;
providing a detector comprising a coupling circuit electrically connected to the electrical energy generator and the ultrasonic vibrator, wherein the coupling circuit:
supplies the electrical energy to the ultrasonic vibrator to drive the ultrasonic vibrator to generate the ultrasonic vibration; and
during the supply of the electrical energy to the ultrasonic vibrator to drive the ultrasonic vibrator to generate the ultrasonic vibration, detects reflected electrical energy reflected from the ultrasonic vibrator;
making a determination by a determination circuit of whether the electrical energy is suitable to drive the ultrasonic vibrator based on the reflected electrical; energy reflected from the ultrasonic vibrator detected by the coupling circuit of the detector; and
controlling the electrical energy generator to generate the electrical energy based on the determination made by the determination circuit.

13. The method of controlling the endoscopic apparatus of claim 12,
wherein the determination is made by comparing the reflected electrical energy detected by the coupling circuit of the detector with a predetermined threshold, and
wherein the controlling of the electrical energy generator comprises controlling the electrical energy generator to stop generation of the electrical energy when it is determined that the reflected electrical energy is greater than or equal to the predetermined threshold.

* * * * *